United States Patent
Meenen et al.

(10) Patent No.: US 6,319,712 B1
(45) Date of Patent: Nov. 20, 2001

(54) BIOHYBRID ARTICULAR SURFACE REPLACEMENT

(75) Inventors: Norbert M. Meenen, Hamburg; Martin Dauner, Esslingen; Heinrich Planck, Nuertingen, all of (DE)

(73) Assignee: Deutsche Institute fur Textil-und Faserforschung Stuttgart, Denkendorf (DE)

( * ) Notice: Subject to any disclaimer, the term of this patent is extended or adjusted under 35 U.S.C. 154(b) by 0 days.

(21) Appl. No.: 09/238,079

(22) Filed: Jan. 26, 1999

(30) Foreign Application Priority Data

Jan. 30, 1998 (DE) ................................. 198 03 673

(51) Int. Cl.⁷ ....................................... C12N 5/00
(52) U.S. Cl. .......................... 435/395; 435/401; 435/402; 623/11
(58) Field of Search .................... 435/395, 401, 435/402; 623/11

(56) References Cited

U.S. PATENT DOCUMENTS

| | | |
|---|---|---|
| 4,365,357 | 12/1982 | Draenert . |
| 4,457,028 | 7/1984 | Draenert . |
| 5,041,138 | 8/1991 | Vacanti . |
| 5,674,292 | 10/1997 | Tucker et al. . |
| 5,700,289 | 12/1997 | Breitbart et al. . |
| 5,736,372 | 4/1998 | Vacanti . |
| 5,855,608 | 1/1999 | Brekke et al. . |
| 5,891,455 | 4/1999 | Sittinger et al. . |
| 5,981,825 | 11/1999 | Brekke . |
| 6,013,856 | 1/2000 | Tucker et al. . |
| 6,028,242 | 2/2000 | Tucker et al. . |

FOREIGN PATENT DOCUMENTS

| | | |
|---|---|---|
| 0714666A1 | 11/1995 | (EP) . |
| 90/12603 | 11/1990 | (WO) . |
| 94/20151 | 9/1994 | (WO) . |
| WO94/26211 | 11/1994 | (WO) . |
| WO95/31157 | 11/1995 | (WO) . |
| WO95/33502 | 12/1995 | (WO) . |
| WO97/14783 | 4/1997 | (WO) . |

*Primary Examiner*—Leon B. Lankford, Jr.
(74) *Attorney, Agent, or Firm*—Pennie & Edmonds LLP

(57) ABSTRACT

The invention relates to a biohybrid articular surface replacement in the form of a three-dimensional, porous carrier, in which cartilage cells can be cultured in vitro and/or in vivo to a three-dimensional cell union and which following cell growth and optionally after tissue development, can be placed on the exposed bone in the vicinity of a defective articular surface, wherein on the side of the carrier intended for engagement with the bone it has an agent for aiding osseous integration.

39 Claims, 1 Drawing Sheet

BIOHYBRID ARTICULAR SURFACE REPLACEMENT

BACKGROUND ART

The invention relates to a biohybrid joint or articular surface replacement.

For the treatment of damaged articular cartilages, e. g. caused by deformities, injuries or degenerative diseases, development work is concentrated on the production of replacement cartilages, which can be implanted in the patient.

Of late processes for producing implants from cell cultures have become known, such as are e. g. described in the Sittinger international patent application WO 94/20151. Cartilage cells are produced in vitro in cavities of a three-dimensional carrier structure.

The Vacanti WO 90/12603 discloses a system for the in vivo neomorphogenesis of cartilage cells from a cell culture.

The cartilage implants known from the prior art suffer from a number of disadvantages.

A reliable fixing in the subchondral bone is important for a completely satisfactory articular replacement surface replacement. For this purpose the implant must be held by complicated suture techniques or fastening clips.

An important problem in the therapy of pathological changes to articular surfaces is the penetration of synovial fluid, whose constituents, such as hyaluronic acid, impair regeneration and growing in. The synovial fluid, which flushes round the inserted implant, prevents an attachment of the cartilage structure to the defect boundaries and to the bone.

The hitherto known cartilage substitute materials for the treatment of articular defects are unable to fulfill the requisite criteria for a successful, durable healing, such as reliable and simple fastening to the bone, rapid growing in, physiological restoration of the articular structure and permanent functionality.

The problem therefore arises of providing an articular surface replacement, which is formed from cartilage cells in a three-dimensional structure, which is simple and reliable to produce under standard biomedical conditions and with existing equipment.

SUMMARY OF THE INVENTION

This problem is solved by a biohybrid articular surface replacement in the form of a three-dimensional, porous carrier, in which cartilage cells can be cultured in vitro and/or in vivo to a three-dimensional cell union and following cell growth, and optionally after the development of tissue, can be placed on the exposed bone in the vicinity of (that is in place of) a defective articular surface and which is characterized in that the carrier, on the side intended for application to the bone, has material for aiding osseous integration.

In the following said material for aiding osseous integration is called bone integration aid.

DETAILED DESCRIPTION OF THE INVENTION

Figure 1:
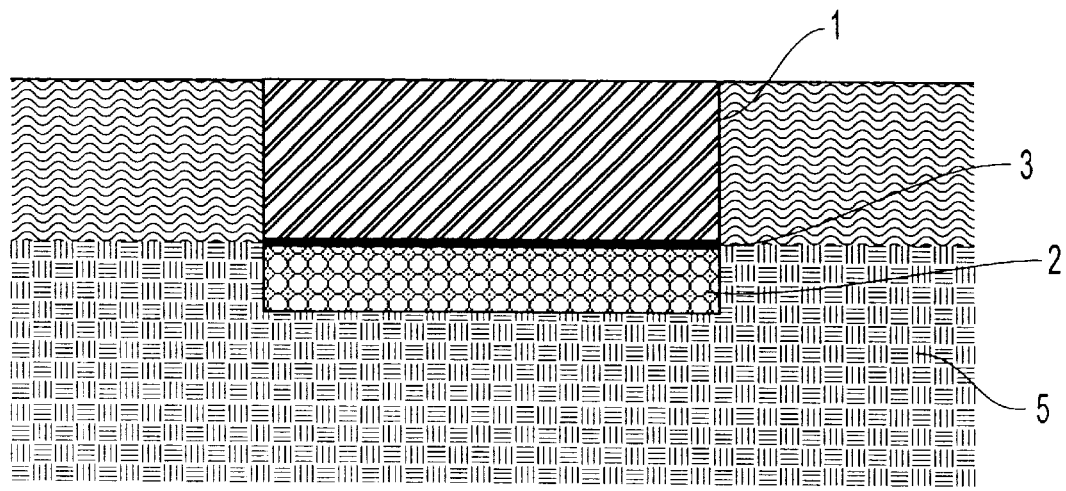
FIG. 1 illustrates a first amendment of an articular surface replacement according to the invention.

For producing replacement cartilage cells, there can firstly be a cellular proliferation of profilating cartilage cells (dedifferentiated, so-called fibroblast-like cells). This can e. g. take place as a flat or a real cell growth in a cell culture vessel. Following a certain proliferation of the cells, the cells are then rendered specific again (differentiated) and introduced into a suitable matrix for further, three-dimensional growth. In particular, the cartilage cells can be injected into the matrix or can be sucked or centrifuged into the matrix under a slight vacuum. Preferably, a few weeks prior to the planned implantation, such a matrix or carrier structure can be provided with autologous cells of the patient.

The porous carrier can in particular be of a material resorbable in the body under physiological conditions. This can have a natural or synthetic origin. Advantageously the porous carrier is in the form of a nonwoven, foam, sponge, sintered material or a textile structure.

The porous carrier of resorbable material can be characterized in that it has a porosity of more than 65%, particularly more than 75%. The carrier is preferably a highly porous carrier. It can have a porosity of more than 90%, preferably more than 95%.

The porous carrier of resorbable material can be formed from hydrolytically degradable polymers, particularly hydrolyzable polymers of α- and β-hydroxycarboxylic acids. Examples of such biodegradable materials are polymers based on polyglycolic acid, polymers of glycolic acid (PGA), polylactides, polymers of L-lactide (P-L-LA), D-lactide (P-D-LA), DL-lactide (P-DL-LA), polydioxanone, polycaprolactone, copolymers and terpolymers of the aforementioned monomers and/or mixtures of the aforementioned polymers. Advantageously use is made of copolymers of glycolic acid and lactic acid in a ratio of 99:1 to 1:99, particularly 89:11 to 70:30 or 30:70 to 11:89. It is also possible to use with advantage copolymers of L-lactide and DLlactide in a ratio of 99:1 to 1:99, more particularly 99:1 to 70:30. The copolymers, terpolymers and/or mixtures of the aforementioned monomers or polymers to be used according to the invention can be provided, for the purpose of improving their characteristics, with plasticizing substances, particularly caprolactone, trimethylene carbonate (TMC) triethyl citrate (TEC) and/or acetyl butyl citrate (AtBC).

Whilst taking the corresponding precautions for preventing immunological problems or infectious diseases, the porous carrier can be made from natural, resorbable substances, advantageously from collagen or hyaluronic acid and derivatives thereof.

The porous carrier can be formed from foam, sponge, sintered material or a textile structure, preference being given to staple fibre or spunbonded fabrics.

In the case of porous carriers made from fibrous materials, such as nonwovens or other textile fabrics, the fibre diameter can advantageously be about 1 to 50 μm, particularly 5 to 15 μm.

For the better control of chondrosis and for influencing the degradation time, porous carriers can be made from a combination of fibrous materials. This can take place by the use of fibre blends, or by mixed fibres, biconstituent fibres or bicomponent fibres. A controlled degradation can advantageously be achieved by the use of bicomponent fibres of the core/jacket or island type.

Laminated carriers (e.g. nonwovens) can have a thickness of about 1 to 5 mm. For example, in the case of implants for use on the knee of a human, layer thicknesses of 1 to 3 mm can be used. For applications to hips, as a result of the higher stressing, greater thicknesses are appropriate.

The articular surface replacement according to the invention can be characterized in that the bone integration aid is firmly bound to the porous carrier. Advantageously the bone integration aid is partially embedded in a sealing agent. Examples of sealing agents suitable in accordance with the invention are films or membranes of resorbable polymers mentioned in connection with the porous carrier.

The bone integration aid can be present in finely divided form, the average particle size being preferably between about 10 and 500 µm, particularly between 50 and 100 µm.

According to the invention the bone integration aid can be present in a quantity, which covers the surface of the side facing the bone by at least about 30 to 100%, preferably 95 to 100%

Advantageously the bone integration aid is formed from an inorganic matrix of the bone and in particular comprises the latter.

Examples of preferred bone integration aids according to the invention are hydroxyapatite ceramic, tricalcium phosphate ceramic, mixed ceramics and/or calcium carbonate. Amorphous forms of inorganic bone matrix materials are also possible.

The bone integration aid can in particular have a porous structure, the porosity being about 30 to 80 vol. % and the pore size of about 10 to 150 µm. The bone integration aid can also comprise a cohesive, highly porous plate.

According to an embodiment of the invention the bone integration aid has a biological origin and in particular comprises high temperature-treated bone. Such a high temperature treatment can in particular take place at temperatures above 1000° C. Bone material treated in this way is a biological hydroxyapatite ceramic.

According to another embodiment of the invention the bone integration aid can be formed from a ceramic having a completely synthetic origin. For producing such a ceramic, experts can use production methods known from the prior art.

For the production of an articular cartilage biohybrid, a cultured articular cartilage in a suitable three-dimensional space structure according to the invention, it is necessary to have a base, which forms with the bone a permanent, non-positive connection. It is in particular possible to use a hydroxyapatite ceramic granular material, which in bioactive and osteoconductive manner aids a rapid, substantial integration by the growing of the interstitial matrix on the synthetic, porous material.

According to the invention the granular material can be incorporated into a resorbable polymer film. The articular surface replacement according to the invention can be characterized in that the particles of the bone integration aid are partly embedded in a layer and part of the surface thereof is exposed. Thus, following the degradation of the polymer constituents of the biohybrid implant, the articular cartilage with its matrix is fixed to a ceramic base, which in turn has a reliable hold in the subchondral bone.

According to the invention the hydroxyapatite ceramic particles can be in a monolayer in a polymer film. As an example for polymer films suitable according to the invention are given films or membranes of resorbable polymers mentioned in conjunction with the porous carrier.

Preference is given to the use of a polymer film having a thickness of approximately 100 to 300 µm. With embedded particles the polymer film can in particular have a thickness of up to 600 µm. The particle size in the monolayer can be 10 to 500 µm, particularly 50 to 100 µm.

The articular surface replacement shall be adapted in an optimal manner to the respective surface of the articular region to be replaced. According to the invention the three-dimensional, porous carrier and/or the bone integration aid can be provided in a concave, convex or any other curved shape adapted to the natural articular cartilage to be replaced. Advantageously the bone integration aid can be flat at the side facing the bone to facilitate the implantation procedure.

The appropriate shape can be determined non-invasively by picture generating diagnosis like X-ray computer tomography and NMR respectively, and be remodelled as a model or a matrix using any rapid prototyping process.

The articular surface replacement according to the present invention can be characterized in that materials can be provided, which protect the contact surface between implant and defect boundaries on the cartilage and between bone integration aid and bone in the implanted state against access or admission of fluid, particularly synovial fluid.

According to the invention the synthetic support structure towards the defect boundary can be defined in such a way that it is impermeable for synovial fluid and cells. This makes it possible to keep away substances impairing a reliable anchoring of the implant in the bone.

According to an embodiment of the invention with respect to the articular surface replacement a sealing layer can be provided for protecting the contact area between implant and defect boundaries on the cartilage and between bone integration aid and bone in the implanted state against the access of fluid. An example of a sealing material suitable according to the invention is constituted by films or membranes from the resorbable polymers mentioned in conjunction with the porous carrier.

In a further embodiment of the invention with respect to the articular surface replacement it is possible to provide a semipermeable membrane for the protection of the contact area between implant and defect boundaries on the cartilage and between bone integration aid and bone in the implanted state against the access of fluid. An example of semipermeable membrane suitable according to the invention is provided by films or membranes of the resorbable polymers mentioned in conjunction with the porous carrier.

The cut-off of such a membrane can in particular be less than 60,000 Dalton. In this way it is possible to prevent larger molecules, such as e.g. proteins, and cells from passing through the membrane.

In yet another embodiment of the invention with respect to the articular surface replacement a microporous membrane with a pore size preferably below 1 µm is provided for protecting the contact area between implant and defect boundary on the cartilage and between bone integration aid and bone in the implanted state against the access of fluid. An example of microporous membrane suitable according to the invention is constituted by microfiber nonwovens or films or membranes from resorbable polymers mentioned in conjunction with the porous carrier.

Advantageously a protecting layer is provided, which in particular forms a barrier for cells and synovial fluid, but which is permeable in such a way as to permit metabolism. For a rapid adhesion and a substantial integration of the implant, an unhindered metabolism is important.

Examples of polymer materials from which it is possible to produce a separating layer, sealing layer, polymer film, closed layer, protective layer, membranes, etc. are constituted by polylactides, polymers of L-lactide (P-L-LA), D-lactide (P-D-LA), DL-lactide (P-DL-LA), polydioxanone, polycaprolactone, copolymers and terpolymers of said monomers and/or mixtures of said polymers, together with copolymers or mixtures of the aforementioned polymers with polyglycolic acid. Advantageously use is made of copolymers of glycolic acid and lactic acid in a ratio of 90:10 to 1:99, particularly 30:70 to 11:89. It is also advantageous to use copolymers of L-lactide and DL-lactide in a ratio of 99:1 to 1:99, particularly 99:1 to 70:30. The copolymers, terpolymers and/or mixtures of the aforementioned monomers or polymers to be used according to the invention can be provided, for the purpose of improving their characteristics, with plasticizing substances, particularly caprolactone, trimethylene carbonate (TMC), triethyl citrate (TEC) and/or acetyl butyl citrate (AtBC).

Whilst taking the corresponding precautions for preventing immunological problems or infectious diseases the separating layer, sealing layer, polymer film, closed layer, protective layer, membranes, etc. can be made from natural, resorbable substances, advantageously from collagen or hyaluronic acid and derivatives therof.

Advantageously the polymers to be used for the inventive separating layers, etc. are processed from a solution. In another embodiment of the invention the polymers to be used for the inventive separating layer can be thermoplastically processable. In another embodiment of the invention the polymers to be used for the inventive separating layer can be processed in crosslinking manner.

The articular surface replacement according to the invention can advantageously be characterized in that the closed layer, at least during the initial growing in time following implantation, is substantially impermeable for fluids.

According to another embodiment the articular surface replacement according to the invention can be characterized in that with it is associated a cover film intended for covering the top side of the carrier remote from the bone integration aid. Advantageously the cover film is fixed to the carrier and is in particular adhesively/cohesively physically associated. Materials for the inventive cover film can be polymer materials, as proposed hereinbefore for the separating layer. The covering film can in particular be of resorbable material. The covering film is preferably constituted by a porous membrane, which prevents any penetration of synovial fluid.

Advantageously the covering film is larger than the surface of the carrier top side and has projecting edges, which serve to cover the separating line between the articular surface replacement and the natural articular cartilage surface.

For fixing the covering film to the porous carrier use is advantageously made of surgical suture material of bioresorbable material. The degradation time of the suture material can be in the range of the degradation time of the resorbable covering film. A reliable fixing can be ensured if the resorption time of the suture material is in particular longer than that of the covering film. Suitable resorption times for the film are e.g. 1 to 4 months. Suture materials according to the invention based on polyglycolic acid are more particularly preferred. Other fixing media are tissue adhesives, resorbable pins or clips or collagen.

Alternatively or in addition to the covering film, with the inventive articular surface replacement can be associated a resorbable sealing compound, which is introduced between the porous carrier and the defect boundary or which is applied to the surface boundary line between implant and articular surface, so as to prevent a penetration of macromolecular constituents of the synovial fluid. The resorbable sealing compound can e.g. be a tissue adhesive or collagen.

Advantageously, in the articular surface according to the present invention the shape of the three-dimensional porous carrier and the bone integration aid can be curved according to the natural articular surface to be replaced. In a particularly preferred embodiment the surface of the bone integration aid facing the bone can be flat.

For use as an implant the articular surface replacement according to the invention is sterilized in an appropriate manner. An appropriate sterilization process can be chosen from conventional physical or chemical methods for inactivating microorganisms or a combination of such methods. One possible sterilization method involves the treatment with ionizing radiation, such as e.g. irradiation with β- or γ-rays in the range of about 0.1 to 10 Mrad, particularly 0.8 to 2.5 Mrad. According to a possible embodiment of the invention a sterilization performed with the aid of irradiation can be simultaneously used for controlling the degradation behaviour of the articular surface replacement produced in accordance with the invention.

In the case of treatment with γ-rays there can be a chain splitting in the case of resorbable polymer material, which improves the resorbability in the body environment, but at the same time leads to no significant loss of strength.

For improving the hydrophilicity of the polymer material modifications can be made to the polymer surface. Advantageously there is a modification of functional groups in the case of a plasma treatment by reactions on the surface of the material. This can also bring about a rise in the hydrophilic properties. According to preferred embodiments such a hydrophiling and/or functionalizing of the surface can be carried out with low temperature plasma. Advantageously the modification reactions are performed in an inert gas atmosphere, oxygen, CO2 and/or SO2. According to another embodiment of the invention a plasma grafting can take place with monomers and/or oligomers for polymer surface modification purposes. A surface modification can facilitate the colonization with cells and consequently favourably influences the growing in of the implant and the regeneration of the treated joint.

To facilitate regeneration after implantation, the implant according to the invention can be provided with growth factors in an effective concentration. It is possible to use both growth factors for cartilage cells, growth factors for bone cells or combinations thereof. Growth factors for bone cells are, according to the invention, preferably incorporated into the film for the integrating agent. Examples are growth factors known in connection with physiology and medicine, such as e.g. osteogenic protein, BFGF (basic fibroblast growth factor), BMP (bone morphogenic protein), rh BMP (re-combinant human bone morphogenic protein), TGF-β (transforming growth factor), IGF (insulin-like growth factor) and EGF (endothelial growth factor). Suitable growth factor concentrations are about 0.1 to 50 ng/ml.

Fluctuations in the pH value can occur during the resorption of the biodegradable polymers used for the inventive biohybrid articular surface replacement. Advantageously basic salts can be introduced into the polymers and/or the pores of the implant for buffering purposes. Examples of buffer salts are calcium carbonate, sodium carbonate, sodium tartrate and/or other buffer systems suitable under physiological conditions. The buffer compounds are advantageously used in a concentration of about 0.1 to 20 wt. %, preferably 1 to 10 wt. %, based on the resorbable polymer weight.

The articular surface replacement according to the invention makes available an implant for restoring a damaged articular cartilage, which permits a culturing of a functional cartilage transplant with autologous cartilage and ensures a reliable anchoring in the subchondral bone. To improve the anchoring of the implant in the bone, it is possible beforehand to punch, mill or cut the defect to size, so that a correspondingly adapted implant structure can be pressed into the same. The implant piece can be preferably cylindrically formed beforehand from a cartilage substitute previously produced in large area form. Advantageously diameters of about 10 to 15 mm are used.

EXAMPLES

Further features and details of the invention can be gathered from the following description of preferred embodiments relative to examples and with reference to the attached drawings. The examples serve to illustrate preferred embodiments and the invention is in no way restricted thereto. Changes and modifications apparent to the expert are possible without leaving the scope of the invention.

Figure 2:
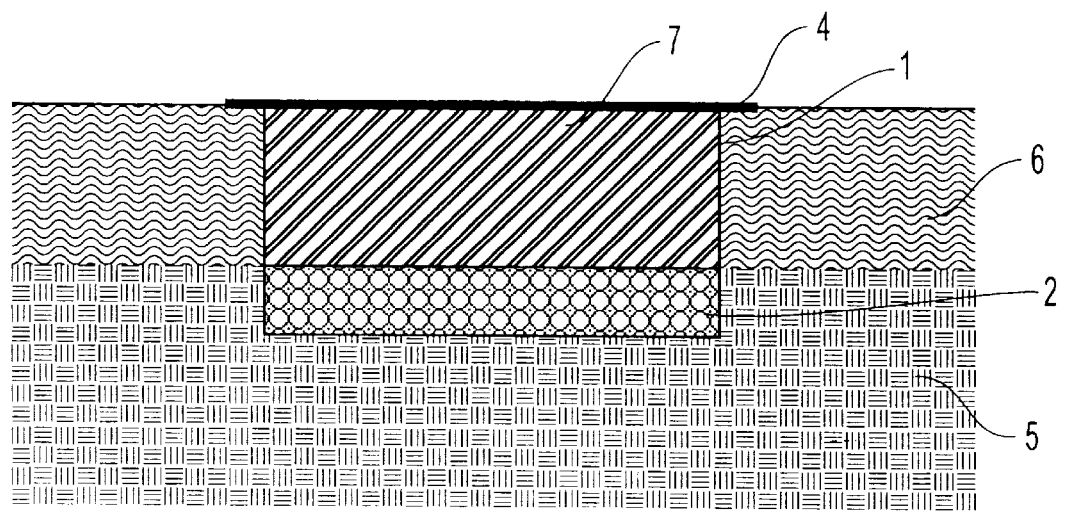
FIG. 2, illustrates a second embodiment of an articular surface replacement according to the invention.

In the drawings FIG. 1 shows an articular surface replacement according to the invention, as illustrated in example 1, whilst FIG. 2 shows an articular surface replacement according to the invention, as illustrated in example 2.

Example 1

A porous carrier 1 is formed as a nonwoven structure from resorbable polymer fibres, produced from a copolymer of glycolic acid and lactic acid. The carrier 1 has a pore volume of 95% and is firmly connected to a bone integration aid 2. Granular hydroxyapatite ceramic with an average particle size of 0.3 mm is used as the bone integration aid. For the connection of porous carrier 1 and bone integration aid 2 is provided a sealing layer 3 of a resorbable polymer membrane, produced from the same copolymer of glycolic acid and lactic acid. The main function of the polymer membrane is to protect the hydroxyapatite ceramic and the subchondral bone 5 located thereunder after implantation from the integration-inhibiting synovial fluid.

Example 2

A porous carrier 1 in accordance with example 1 is provided with a covering layer 4 of a resorbable polymer membrane, produced from a polyglycolidetrimethylene carbonate copolymer. The polymer membrane is firmly connected to the porous carrier 1 by a central button suture, produced with resorbable suture material from polyglycolic acid. The membrane covers the fitting gap 7 of the pressed in implant and is suitable, following a corresponding fixing to the surrounding cartilage 6, for protecting the complete implant and connecting body tissue against the penetration of integration-inhibiting synovial fluid. The bone integration aid 2 comprises a plate of porous hydroxyapatite ceramic, which permits a particularly firm, primary anchoring in the case of a corresponding preparation of the implant location.

What is claimed is:

1. A biohybrid articular surface replacement device comprising a three dimensional, porous carrier suitable for culturing cartilage cells to a three-dimensional cell union, wherein the device has suitable dimensions allowing it to be placed, optionally following cell growth and optionally after tissue development, on an exposed bone in place of a defective articular surface, wherein on a side of the porous carrier intended for engagement with the bone a bone integration aid is provided, the device further comprising means for protecting the area between the bone integration aid and bone from access or admission of fluid.

2. The articular surface replacement device according to claim 1, wherein the porous carrier is made of resorbable material.

3. The articular surface replacement device according to claim 1, wherein the porous carrier comprises at least one resorbable, hydrolytically degradable, synthetic polymer.

4. The articular surface replacement device according to claim 1, wherein the porous carrier is formed from one of the group consisting of a sponge, foam, sintered material and a textile structure.

5. The particular surface replacement device according to claim 4, wherein the textile structure is one of the group consisting of a staple fiber and a spunbonded fabric.

6. The articular surface replacement device according to claim 1, wherein the bone integration aid is firmly bound to the porous carrier.

7. The articular surface replacement device according to claim 1, wherein the bone integration aid is in finely divided form.

8. The articular surface replacement device according to claim 7, wherein the bone integration aid comprises particles with an average particle size between about 10 $\mu$m and about 500 $\mu$m.

9. The articular surface replacement device according to claim 1, wherein the bone integration aid comprises a cohesive, highly porous plate.

10. The articular surface replacement device according to claim 1, wherein the bone integration aid covers up to about 30% to about 100% the surface of the side facing the bone.

11. The articular surface replacement device according to claim 1, wherein the bone integration aid comprises an inorganic bone matrix material.

12. The articular surface replacement device according to claim 1, wherein the bone integration aid is formed from an inorganic bone matrix material.

13. The articular surface replacement device according to claim 11, wherein the inorganic bone matrix material comprises at least one ceramic material selected from the group consisting of hydroxyapatites, tricalcium phosphates, mixed calcium phosphate and calcium carbonate.

14. The articular surface replacement device according to claim 11, wherein the inorganic matrix material comprises at least one amorphous material selected from the group consisting of hydroxypatites, tricalcium phosphates, mixed calcium phosphates and calcium carbonate.

15. The articular surface replacement device according to claim 1, wherein the bone integration aid is of biological origin.

16. The articular surface replacement device according to claim 15, wherein the bone integration aid comprises a high temperature-treated bone.

17. The articular surface replacement device according to claim 1, wherein the bone integration aid has a porous structure.

18. The articular surface replacement device according to claim 17, wherein the bone integration aid has a porosity, of about 30 vol. % to about 80 vol. %.

19. The articular surface replacement device according to claim 17, wherein the bone integration aid has a pore size, of about 10 $\mu$m to about 150 $\mu$m.

20. The articular surface replacement device according to claim 1, wherein the protecting means comprise a closed layer positioned upon the three-dimensional porous carrier.

21. The articular surface replacement device according to claim 8, wherein the protecting means comprise a film or membrane on which particles of the bone integration aid are anchored.

22. The articular surface replacement device according to claim 21, wherein the film or membrane is resorbable.

23. The articular surface replacement device according to claim 21, wherein the film or membrane covering is positioned upon a topside of the three-dimensional porous carrier.

24. The articular surface replacement device according to claim 1, wherein the articular surface replacement device is an implant for implanting onto a natural articular surface.

25. The articular surface replacement device according to claim 23, wherein the film or membrane covering encompasses a contact gap between the implant and the natural articular surface.

26. The articular surface replacement device according to claim 23, wherein the film or membrane covering is resorbable.

27. The articular surface replacement device according to claim 25, wherein the film or membrane covering is resorbable.

28. The articular surface replacement device according to claim 24, wherein the protecting means comprise a resorbable sealing compound.

29. The articular surface replacement device according to claim 1, wherein the shape of the three-dimensional porous carrier and the bone integration aid is adapted to that of the natural articular surface to be replaced.

30. The articular surface replacement device according to claim 28, wherein the surface of the bone integration aid facing the bone is flat.

31. The articular surface replacement device according to claim 3, wherein the synthetic polymer is formed from polyesters of α-hydrocarboxylic acids.

32. The articular surface replacement device according to claim 1, wherein the bone integration aid is firmly bound to the porous carrier's side which is engaged with the bone.

33. The articular surface replacement device according to claim 1, wherein the bone integration aid covers from about 30% to about 100% of the carrier's side facing the bone.

34. The articular surface replacement device according to claim 1, wherein the porous carrier comprises at least one resorbable, hydrolytically degradable, synthetic polymer.

35. The articular surface replacement device according to claim 34, wherein the synthetic polymer is formed from polyesters of α-hydrocarboxylic acids.

36. The articular surface replacement device according to claim 1, wherein the porous carrier and the bone integration aid are in the form of a layered structure.

37. The articular surface replacement device according to claim 28, wherein the resorbable sealing compound is introduced between the implant and an implant support layer.

38. The articular surface replacement device according to claim 28, wherein the resorbable sealing compound is applied to a surface between the implant and the articular surface.

39. The articular surface replacement device according to claim 38, wherein the resorbable sealing compound is applied to prevent penetration of macromolecular constituents of synovial fluid.

* * * * *